United States Patent
Mhaske et al.

(10) Patent No.: US 9,650,330 B2
(45) Date of Patent: May 16, 2017

(54) PROCESS FOR THE SYNTHESIS OF ARYL SULFONES

(71) Applicant: Council of Scientific and Industrial Research, New Delhi (IN)

(72) Inventors: Santosh Baburao Mhaske, Pune (IN); Virat Pandya, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/103,567

(22) PCT Filed: Dec. 12, 2014

(86) PCT No.: PCT/IN2014/000772
§ 371 (c)(1),
(2) Date: Jun. 10, 2016

(87) PCT Pub. No.: WO2015/087352
PCT Pub. Date: Jun. 18, 2015

(65) Prior Publication Data
US 2016/0304447 A1    Oct. 20, 2016

(30) Foreign Application Priority Data
Dec. 12, 2013  (IN) .......................... 3617/DEL/2013

(51) Int. Cl.
| | | |
|---|---|---|
| *C07C 315/04* | (2006.01) |
| *C07C 317/14* | (2006.01) |
| *C07C 317/22* | (2006.01) |
| *C07D 317/46* | (2006.01) |
| *C07D 333/34* | (2006.01) |

(52) U.S. Cl.
CPC .......... *C07C 315/04* (2013.01); *C07C 317/14* (2013.01); *C07C 317/22* (2013.01); *C07D 317/46* (2013.01); *C07D 333/34* (2013.01)

(58) Field of Classification Search
CPC ..................................................... C07C 315/04
USPC ........................................................ 549/434
See application file for complete search history.

(56) References Cited

PUBLICATIONS

Cacchi et al: "Unsymmetrical diaryl sulfones and arylvinylsulfones through Palladium-catalyted coupling of aryl and vinyl halides or triflates with sulfinic acid salts", Journal of Organic Chemistry, vol. 69, 2004, pp. 5608-5614.
International Search Report for PCT/IN2014/000772 dated Apr. 7, 2015.
International Preliminary Report on Patentability (IPRP) for PCT/IN2014/000772 dated Nov. 11, 2015.
Ni et al: "Nucleophilic fluoroalkylation of alpha,beta-enones,arynes and activated alkynes with fluorinated sulfones: probing the hard/soft nature of fluorinated carbanions", Journal of Organic Chemistry, vol. 73, 2008, pp. 5699-5713.
Pandya et al: "Transition-Metal free C—S bond formation: a facile access to aryl sulfones from sodium sulfonates via arynes", Organic Letters, vol. 16, 2014, pp. 3836-3838.
Yoshioka et al: "Insertion of arynes into the carbonoxygen double bond of amides and its application into the sequential reactions", Tetrahedron, Elsevier Science Publishers, vol. 68. No. 1, Oct. 20, 2011 (Oct. 20, 2011), pp. 179-189.

*Primary Examiner* — Taofiq A Solola
(74) *Attorney, Agent, or Firm* — Fish & Richardson P.C.

(57) ABSTRACT

The present patent discloses a novel, efficient and transition-metal-free room temperature single step process for synthesis of aryl sulfones and substituted aryl sulfones starting from aryl substrates.

7 Claims, No Drawings

PROCESS FOR THE SYNTHESIS OF ARYL SULFONES

FIELD OF THE INVENTION

The present invention relates to a novel, efficient and transition-metal-free process for the preparation of aryl sulfones.

BACKGROUND AND PRIOR ART OF THE INVENTION

Arylsulfones are important building blocks in organic chemistry and especially in medicinal chemistry. The arylsulfone fragment is found in various drugs, such as the COX-2 inhibitor Vioxx or the prostaglandin $D_2$ antagonist Laropiprant. Diarylsulfones have been shown to exhibit antitumor activities or to inhibit HIV-1 reverse transcriptase.

Because of their importance, numerous procedures for the synthesis of arylsulfones have been reported, such as the oxidation of sulfides, the sulfonylation of arenes, or Pd- and Cu-catalyzed coupling reactions as well as transition-metal-free synthesis of diarylsulfones from arylsulfinic acid sodium salts and diaryliodonium salts.

Article titled, "Arylation of Lithium Sulfinates with Diaryliodonium Salts: A Direct and Versatile Access to Arylsulfones" by Natalie Umierski and Georg Manolikakes in Organic Letters 2013, 15, 188 reports an efficient, transition-metal-free arylation of lithium sulfinates, which are readily accessible from reactions of organolithium reagents with sulfurdioxide. Based on this method, it further reports a practical protocol for the direct transformation of (hetero) arenes and (hetero)aromatic halides into diarylsulfones.

U.S. Pat. No. 3,250,812 discloses a process for producing alkyl aryl sulfones which comprises reacting an aryl compound having free hydrogen on the ring with a compound having the formula (RiSO2)2O, wherein R1 is a lower alkyl radical in a solvent at sufficient temperatures to effect said reaction.

U.S. Pat. No. 4,386,221 disclose a process for the preparation of aryl alkyl sulfones and aryl vinyl sulfones. The process comprises of reacting an aryl compound with an alkyl sulfonyl fluoride or with a vinyl sulfonyl fluoride in the presence of a catalyst selected from AlCl3 and AlBr3.

U.S. Pat. No. 5,015,775 discloses Alkyl aryl sulfones of the formula R—SO3—Ar-Yn, wherein Ar is an aryl compound, Y is a substituent on the aryl compound and R is alkyl or cycloalkyl, and liquid mixtures of positional isomers of the same are prepared by reacting an aryl compound of the formula Ar-Yn, with an alkyl sulfonic acid of the formula R—SO3H and a phosphorus reagent, preferably under heat.

Article titled, "One-step synthesis of α,β-unsaturated arylsulfones by a novel multicomponent reaction of aromatic aldehydes, chloroacetonitrile, benzenesulfinic acid sodium salt" by Lei Zhang, Mao Hua Ding, Hong Yun Guo in Chinese Chemical Letters, Volume 23, Issue 12, December 2012, Pages 1352-1354 reports a new and green method for the synthesis of α,β-unsaturated arylsulfones through the condensation of aromatic aldehydes, chloroacetonitrile, benzenesulfinic acid sodium salt in the presence of 1-butyl-3-methyl imidazolium hydroxide ([bmim]OH) in EtOH under reflux. The ionic liquid was recovered and recycled for subsequent reactions. The advantages of this protocol were non-toxic, easy work-up and good yields.

Article titled, "A mild and efficient new synthesis of aryl sulfones from boronic acids and sulfinic acid salts" by Christian Beaulieu, Daniel Guay, Zhaoyin Wang and David A. Evans in Tetrahedron Letters 45 (2004) 3233-3236 reports a new efficient and mild preparation of sulfones from boronic acids and sulfinic acid salts. The cross-coupling reaction mediated by cupric acetate gives access to a variety of sulfones in excellent yield.

Article titled, "Synthesis of Aryl Sulfones via 1-Proline-Promoted CuI-Catalyzed Coupling Reaction of Aryl Halides with Sulfinic Acid Salts" by Wei Zhu and Dawei Ma in *J. Org. Chem.*, 2005, 70 (7), pp 2696-2700 reports The CuI/I-proline sodium salt catalyzed coupling reaction of aryl halides with sulfinic acid salts readily occurs at 80-95° C. in DMSO to give the corresponding aryl sulfones in good to excellent yields. This process is well-tolerated by a wide range of functional groups including hydroxyl, amino, acetanilide, ketone, ester, and nitrile. Using this method, 4-phenylsulfonyl- and 4-methanesulfonyl-substituted 1-phenylalanine derivatives are prepared.

U.S. Pat. No. 5,468,903 relates to a process for preparing a compound comprising a monocyclic aromatic ring having at least a first substituent and a substituted sulphonyl group at the position para to the first substituent, the process comprising mixing a reactant comprising the monocyclic aromatic ring with the first substituent and hydrogen in the position of the ring para to the first substituent, with a sulphonic acid halide derivative in the presence of a naturally occurring or synthetic zeolite capable of catalyzing a sulphonylation reaction between the reactant and the sulphonic acid halide.

U.S. Pat. No. 6,455,738 B1 relates to a process for the sulfonation of an aromatic compound, said process comprising the steps of:
 a) reacting said aromatic compound with a sulfonating agent, in the presence of a catalytically effective amount of a catalyst which is a mixture of bismuth trihalide and of perfluoroalkanesulfonic acid, with a molar ratio less than the stoichiometry resulting in the complete exchange of the halide by the sulfonic functional group, to obtain a sulfonated aromatic compound, and
 b) recovering the sulfonated aromatic compound obtained in step (a).

U.S. Pat. No. 4,950,793 discloses a process of reacting an aromatic hydrocarbon with a halogenated sulfonic acid in the presence of a Lewis acid to obtain an aromatic sulfone compound.

U.S. Pat. No. 5,276,196 relates to the synthesis of bis (haloarylsulfonyl) aromatic compounds and more specifically, bis(chlorophenylsulfonyl) aromatic compounds. A process has been reported wherein product of high purity and minimal iron contamination is produced by reacting haloarylsulfonyl halide with an aromatic compound in the presence of an appropriate catalyst with and without solvent.

U.S. Pat. No. 2,743,290 relates to a process for the production of halogenated thioesters of a sulfonic acid.

However, till date arynes have not been used for such transformation.

OBJECTIVE OF THE INVENTION

The main object of the present invention is to provide a room temperature single step process for synthesis of aryl sulfones and substituted aryl sulfones starting from aryl/aryl substrates.

SUMMARY OF THE INVENTION

The present invention provides a room temperature single step process for synthesis of compound of Formula I

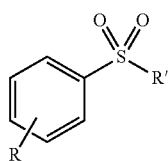

Formula I wherein, R is selected from H, alkyl ($C_1$-$C_6$), aryl, heteroaryl, O-, S-, N-, P-alkyl/unsubstituted and substituted aryl;
R' is selected from alkyl ($C_1$-$C_6$), aryl, heteroaryl, O-, S-, N-, P-alkyl/unsubstituted and substituted aryl;
comprising the steps of:
a. adding benzyne precursor of Formula II to a stirred solution of fluoride ion source and compound of Formula III in the ratio ranging between 1:1 to 1:1.1 in anhydrous acetonitrile to obtain a reaction mixture;

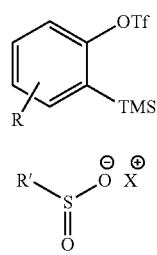

Formula II

Formula III wherein, R is selected from H, alkyl, aryl, heteroaryl, O-, S-, N-, P-alkyl/unsubstituted and substituted aryl;
R' is selected from, alkyl, aryl, heteroaryl, O-, S-, N-, P-alkyl/unsubstituted and substituted aryl;
X is selected from H, Li, Na, K, Cs;
b. stirring the reaction mixture of step (a) for the period in the range of 1 to 8 hours followed by purification to obtain the desired product.

In an embodiment of the present invention, fluoride ion source is selected from the group consisting of TBAF (Tetra-n-butylammonium fluoride), CsF (Cesium fluoride), NaF (Sodium Fluoride), RbF (Rubidium fluoride) or KF (Potassium fluoride).

In yet another embodiment of the present invention, the fluoride ion source is selected from TBAF or CsF.

In another embodiment of the present invention, compound of formula I is selected from the group consisting of:
1-Phenyl(sulfonyl)benzene (3);
1,2-Difluoro-4-(phenylsulfonyl)benzene (5);
1,2-Dimethyl-4-(phenylsulfonyl)benzene (7);
1,4-Dimethyl-2-(phenylsulfonyl)benzene (9);
1-Methoxy-3-(phenylsulfonyl)benzene (11);
1,3-Dimethoxy-5-(phenylsulfonyl)benzene (13);
1,2-Dimethoxy-4-(phenylsulfonyl)benzene (15);
5-(Phenylsulfonyl)benzo[d][1,3]dioxole (17);
(Methylsulfonyl)benzene (19);
(Butylsulfonyl)benzene (21);
1-Methyl-4-(phenylsulfonyl)benzene (23);
1-(Tert-butyl)-4-(phenylsulfonyl)benzene (25);
1-Methoxy-4-(phenylsulfonyl)benzene (27);
1-(4-(phenylsulfonyl)phenyl)ethan-1-one (29);
1-Nitro-4-(phenylsulfonyl)benzene (31);
1-Fluoro-4-(phenylsulfonyl)benzene (33);
2-bromo-5-(phenylsulfonyl)thiophene (35).

In yet another embodiment of the present invention, compound of formula II is selected from the group consisting of:
2-(trimethylsilyl)phenyl trifluoromethane-sulfonate (1)
4,5-difluoro-2-(trimethylsilyl)phenyl trifluoromethane-sulfonate (4)
4,5-dimethyl-2-(trimethylsilyl)phenyl trifluoromethane-sulfonate (6)
3,6-dimethyl-2-(trimethylsilyl)phenyl trifluoromethane-sulfonate (8)
3-methoxy-2-(trimethylsilyl)phenyl trifluoromethane-sulfonate (10)
3,5-dimethoxy-2-(trimethylsilyl)phenyl trifluoromethane-sulfonate (12)
4,5-dimethoxy-2-(trimethylsilyl)phenyl trifluoromethane-sulfonate (14)
6-(trimethylsilyl)benzo[d][1,3]dioxol-5-yl trifluoromethane-sulfonate (16)

In yet another embodiment of the present invention, compound of formula III is selected from the group consisting of:
sodium benzenesulfinate (2)
sodium methanesulfinate (18)
sodium butane-1-sulfinate (20)
sodium 4-methylbenzenesulfinate (22)
sodium 4-(tert-butyl)benzenesulfinate (24)
sodium 4-methoxybenzenesulfinate (26)
sodium 4-acetylbenzenesulfinate (28)
sodium 4-nitrobenzenesulfinate (30)
sodium 4-fluorobenzenesulfinate (32)
Sodium 5-bromothiophene-2-sulfinate (34).

In yet another embodiment of the present invention, the yield of the compound of formula I is in the range of 45-96%.

DETAILED DESCRIPTION OF THE INVENTION

For the purposes of this patent application, "Room temperature" means temperature in the range of 20-30° C.

Present invention provides a transition metal free process for the synthesis of arylsulfones, wherein sulfinic acid/sulfinic acid salt is treated with arynes to obtain arylsulfones under mild reaction condition, in high yields.

Further, the present invention provides a process for the synthesis of arylsulfones which works with all kinds of aryl substrates having electron donating or withdrawing functional groups.

The process of the present invention provides aryl-aryl sulfones as well as aryl-alkyl sulfones.

Present invention provides a room temperature single step process for synthesis of aryl sulfones and substituted aryl sulfones compound of Formula I

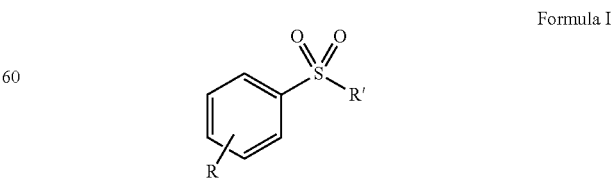

Formula I wherein, R is selected from H, alkyl, aryl, heteroaryl, O-, S-, N-, P-alkyl/unsubstituted and substituted aryl;

R' is selected from alkyl, aryl, heteroaryl, O-, S-, N-, P-alkyl/unsubstituted and substituted aryl,
starting from compounds of Formula II and Formula III,

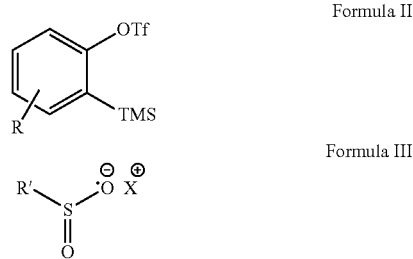

Formula II

Formula III

Wherein, R is selected from H, alkyl, aryl, heteroaryl, O-, S-, N-, P-alkyl/unsubstituted and substituted aryl;
R' is selected from, alkyl, aryl, heteroaryl, O-, S-, N-, P-alkyl/unsubstituted and substituted aryl; and
X is selected from H, Li, Na, K, Cs;
comprising the steps of:
a. adding benzyne precursor of Formula II to a stirred solution of fluoride ion source and compound of Formula III in anhydrous acetonitrile to obtain a reaction mixture;
b. stirring the reaction mixture of step (a) followed by purification affords a solid or thick oil sulfone I.

The process is shown below in Scheme A:

Scheme: A

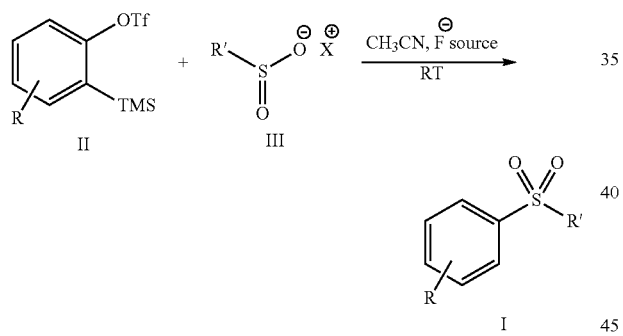

The present invention provides a room temperature single step process for synthesis of aryl sulfones and substituted aryl sulfones compounds of Formula I wherein the fluoride ion source is selected from TBAF, CsF, NaF, RbF, KF and preferably from TBAF or CsF.

The present invention provides a room temperature single step process for synthesis of sulfones and substituted sulfones compounds of Formula I wherein the yield is more than 45% and preferably more than 80%.

In an aspect, the present invention provides the optimization results of fluoride source, various silyl triflate and sulfinates substrates selected which are summarized below in table 1, 2 and 3:

TABLE 1

Optimization studies[a]

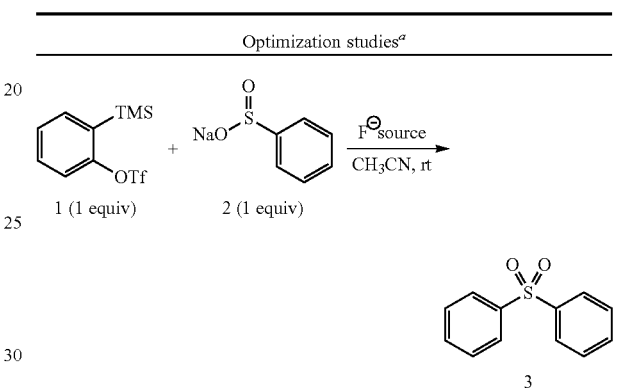

| entry | F⁻ source | equiv | additive[b] | time | Yield |
|---|---|---|---|---|---|
| 1 | CsF | (5.5) | — | 6.0 h | 86% |
| 2 | CsF | (2.5) | A | 6.0 h | 88% |
| 3 | CsF | (2.0) | A | 7.0 h | 82% |
| 4 | CsF | (1.5) | A | 7.0 h | 56% |
| 5 | KF | (2.0) | A | 6.0 h | 67% |
| 6 | TBAF | (2.5) | — | 1.5 h | 95% |
| 7 | TBAF | (1.5) | — | 2.5 h | 94% |
| 8 | TBAF | (1.1) | — | 3.0 h | 94% |
| 9 | TBAF | (1.0) | — | 5.0 h | 72% |

[a]All the reactions were performed on 25 mg scale of o-silyl aryl triflate 1.
[b]A = 18-crown-6-ether (5 mol %).

TABLE 2

Preparation of sulfones from various silyl triflates[a]

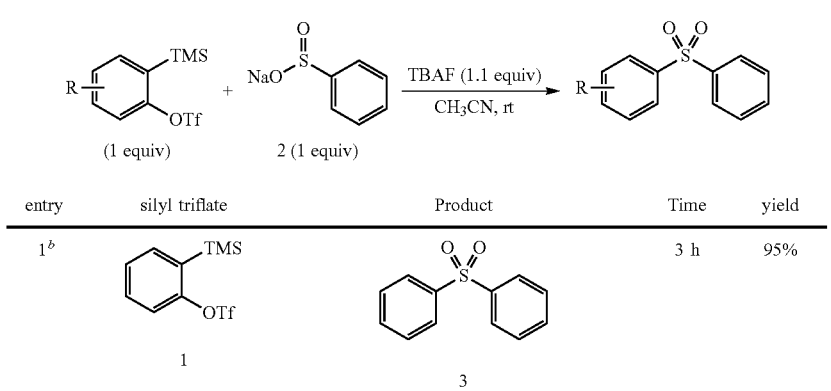

| entry | silyl triflate | Product | Time | yield |
|---|---|---|---|---|
| 1[b] | 1 | 3 | 3 h | 95% |

TABLE 2-continued

Preparation of sulfones from various silyl triflates[a]

| entry | silyl triflate | Product | Time | yield |
|---|---|---|---|---|
| 2 | 4 (4,5-difluoro) | 5 | 6 h | 76% |
| 3 | 6 (4,5-dimethyl) | 7 | 4 h | 92% |
| 4 | 8 (3,6-dimethyl) | 9 | 8 h | 55% |
| 5 | 10 (3-methoxy) | 11 | 4 h | 64% |
| 6 | 12 (3,5-dimethoxy) | 13 | 4 h | 86% |
| 7 | 14 (4,5-dimethoxy) | 15 | 3 h | 60% |
| 8 | 16 (methylenedioxy) | 17 | 6 h | 96% |

[a]All the reactions were performed on 50 mg scale of o-silyl aryl triflates.
[b]This reaction was also performed on 500 mg scale of o-silyl aryl triflate 1.

TABLE 3

Preparation of sulfones from various sulfinates[a]

| Example | NaO−S(=O)−Ar/R | product | time | yield |
|---|---|---|---|---|
| 1 | 18: NaO−S(=O)−CH₃ | 19: Ph−SO₂−CH₃ | 4 h | 75% |
| 2 | 20: NaO−S(=O)−Butyl | 21: Ph−SO₂−Butyl | 8 h / 3 h | 45%[b] / 86%[c] |
| 3 | 22: NaO−S(=O)−C₆H₄−CH₃ | 23: Ph−SO₂−C₆H₄−CH₃ | 3 h | 68% |
| 4 | 24: NaO−S(=O)−C₆H₄−tBu | 25: Ph−SO₂−C₆H₄−tBu | 4 h | 85% |
| 5 | 26: NaO−S(=O)−C₆H₄−OMe | 27: Ph−SO₂−C₆H₄−OMe | 1 h | 61% |
| 6 | 28: NaO−S(=O)−C₆H₄−C(=O)CH₃ | 29: Ph−SO₂−C₆H₄−C(=O)CH₃ | 4 h | 54% |
| 7 | 30: NaO−S(=O)−C₆H₄−NO₂ | 31: Ph−SO₂−C₆H₄−NO₂ | 3 h | 74% |

Reaction scheme: 1 (1 equiv, 2-(trimethylsilyl)phenyl triflate) + NaO−S(=O)−Ar/R (1 equiv) → product, with TBAF (1.1 equiv), CH₃CN, rt.

TABLE 3-continued

Preparation of sulfones from various sulfinates[a]

| Example | NaO–S(=O)–Ar/R | product | time | yield |
|---|---|---|---|---|
| 8 | (sodium 4-fluorobenzenesulfinate) 32 | (phenyl 4-fluorophenyl sulfone) 33 | 3 h | 86% |
| 9 | (sodium 5-bromothiophene-2-sulfinate) 34 | (phenyl 5-bromothiophen-2-yl sulfone) 35 | 3 h | 73% |

[a]All the reactions were performed on 50 mg scale of o-silyl aryl triflate 1.
[b]TBAF (6 equiv).
[c]CsF (4 equiv), 18-crown-6-ether.

EXAMPLES

Following examples are given by way of illustration and therefore should not be construed to limit the scope of the invention.

General Information

All reagents and solvents were used as received from commercial sources unless and otherwise noted. Acetonitrile was dried and stored over 4 Å molecular sieves. All experiments were carried out under an atmosphere of Argon. o-Silyl aryl triflates were synthesized by known procedures. Sodium sulfinates 2 and 18 were purchased from commercial sources and rest of the sodium sulfinates were prepared using known literature procedures. Pre-coated plates (silica gel 60 PF254, 0.25 mm or 0.5 mm) were utilized for Thin Layer Chromatography (TLC). Column chromatographic purifications were carried out on flash silica-gel (240-400 mesh) using petroleum ether and ethyl acetate as eluents. The $^1$H, $^{13}$C, NMR spectra were recorded on 200/400/500 MHz, 50/100/125 MHz NMR spectrometer respectively in $CDCl_3$. Chemical shifts were reported as δ values from standard peaks. Melting point was recorded on Buchi instrument. Mass spectra were taken on LC-MS (ESI) mass spectrometer. HRMS were scanned at NCL, Pune.

Example 1

Experimental Procedure for the Preparation of Sodium Sulfinates

4-Methoxybenzenesulfinic acid sodium salt (26) was prepared by heating of sodium sulfite (2.5 g, 20 mmol), 4-methoxybenzenesulfonyl chloride (2.06 g, 10 mmol) and sodium bicarbonate (1.68 g, 20 mmol) in water (9.6 mL) at 70-80° C. for 4 h. After cooling to room temperature (20-30° C.), water was removed under vacuum and the residue was extracted in ethanol. Recrystallization from ethanol furnished sodium sulfinate 26 (1.34 g, 67%) as a white solid.

The other sodium sulfinates 20, 22, 24, 28, 30, 32 and 34 were prepared similarly from their corresponding sulfonyl chlorides using known methods.

General Experimental Procedure for the Synthesis of Sulfones

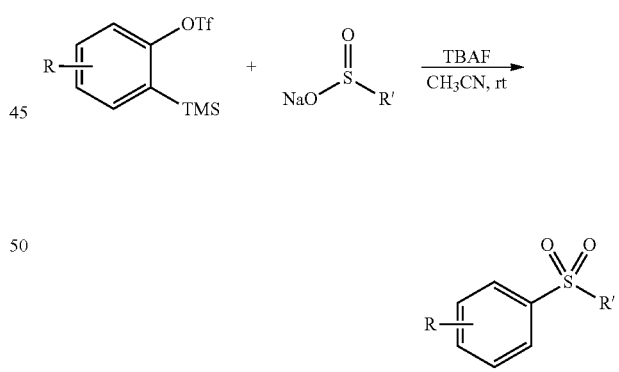

To a round-bottom flask containing TBAF (1.10 equiv) and sodium sulfinate (1.0 equiv) was added o-silylaryl triflate (1.00 equiv) in acetonitrile (1 mL) at room temperature (20-30° C.), under Argon atmosphere. The reaction mixture was stirred at room temperature (20-30° C.) and the progress was monitored by TLC. After completion of the reaction, acetonitrile was removed on rotary evaporator and the crude product was purified by flash silica gel column using a gradient of ethyl acetate-petroleum ether to afford the corresponding diaryl/aryl-alkyl/aryl-heteroaryl sulfones in good to excellent yields.

Example 2

Experimental Procedure Using CsF

(Butylsulfonyl)benzene (21)

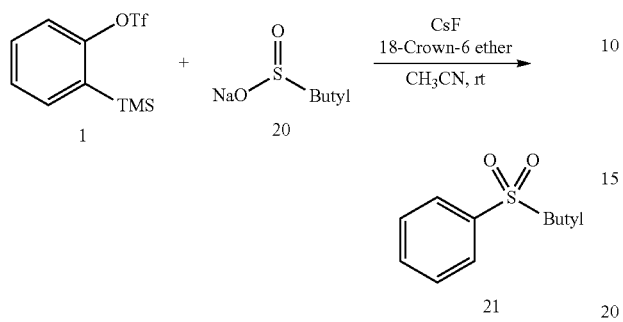

To a round-bottom flask containing CsF (101 mg, 670 mmol) butyl sulfinic acid sodium salt (36.2 mg, 251 mmol) and 18-Crown-6-ether (4.4 mg, 16.7 mmol) was added o-silyl aryl triflate (50 mg, 167.5 mmol) in acetonitrile (2 mL) at room temperature (25° C.), under Argon atmosphere. The reaction mixture was stirred at room temperature (25° C.) and the progress was monitored by TLC. After completion of the reaction (3 h), acetonitrile was removed on rotary evaporator and the crude product was purified by flash silica gel column using a gradient of ethyl acetate-petroleum ether (1:4) to afford the sulfone 21 (29 mg, 86%) as a yellow thick oil.

Example 3

Large Scale Experiment

Sulfone 3, Table 2, Entry 1

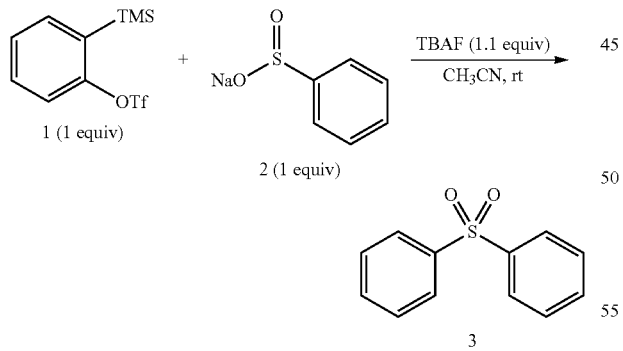

To a round-bottom flask containing TBAF (581 mg, 1.84 mol, 1.10 equiv) and aryl sulfinic acid sodium salt (275 mg, 1.67 mol, 1.0 equiv) was added o-silyl aryl triflate (500 mg, 1.67 mol, 1.0 equiv) in acetonitrile (10 mL) at room temperature (30° C.), under Argon atmosphere. The reaction mixture was stirred at room temperature (30° C.) and the progress was monitored by TLC. After completion of the reaction (3 h), acetonitrile was removed on rotary evaporator and the crude product was purified by flash silica gel column using a gradient of ethyl acetate-petroleum ether (3:17) to afford the sulfone 3 (260 mg, 95%) as a white solid.

Characterization Data of Compounds

All reactions were performed on 50 mg scale of o-silyl aryl triflates. Representative large scale experiment was performed on 500 mg scale of o-silyl aryl triflates.

Example 4

1-Phenyl (sulfonyl) benzene (3)

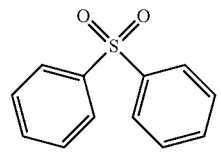 [SMILES: O=S(=O)(c1ccccc1)c1ccccc1]

Reaction Time: 3 h; Rf: 0.3 (1:4 EtOAc: Pet Ether); White solid; 34 mg, 94%; mp 120° C.; $^1$H NMR (400 MHz, CDCl$_3$) δ 7.88 (d, J=8.0 Hz, 4H), 7.50 (t, J=8.0 Hz, 2H), 7.44 (t, J=8.0 Hz, 4H); $^{13}$C NMR (125 MHz, CDCl$_3$) δ 141.6, 133.2, 129.3, 127.7; HRMS-ESI (m/z) calcd [C$_{12}$H$_{10}$O$_2$S+H]$^+$: 219.0474. found: 219.0474.

Example 5

1,2-Difluoro-4-(phenylsulfonyl)benzene (5)

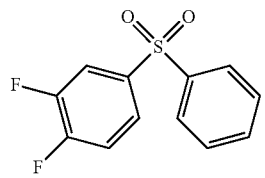 [SMILES: O=S(=O)(c1ccccc1)c1ccc(F)c(F)c1]

Reaction Time: 6 h; Rf: 0.3 (1:4 EtOAc:Pet Ether); White solid; 28.9 mg, 76%; mp 179-181° C. $^1$H NMR (400 MHz, CDCl$_3$) δ 7.86 (d, J=8.2 Hz, 2H), 7.75-7.65 (m, 2H), 7.54 (t, J=8.0 Hz, 1H), 7.47 (t, J=8.0 Hz, 2H), 7.18-7.28 (m, 1H); $^{13}$C NMR (100 MHz, CDCl$_3$) δ 153.6 (dd, J=257.8, 12.4 Hz), 150.3 (dd, J=255.9, 17.2 Hz), 140.8, 138.5 (t, J=7.6 Hz), 133.7, 129.5, 127.7, 124.8 (q, J=3.84 Hz), 118.4 (d, J=18.2 Hz), 111.7 (d, J=18.2 Hz); HRMS-ESI (m/z) calcd [C$_{12}$H$_8$O$_2$SF$_2$Na]$^+$: 277.0105. found: 277.0100.

Example 6

1,2-Dimethyl-4-(phenylsulfonyl)benzene (7)

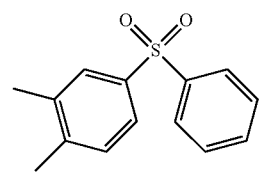 [SMILES: Cc1ccc(S(=O)(=O)c2ccccc2)cc1C]

Reaction Time: 4 h; Rf: 0.3 (1:4 EtOAc:Pet Ether); White solid; 34.7 mg, 92%; mp 114-116° C.; $^1$H NMR (400 MHz, CDCl$_3$) δ 7.86 (d, J=7.3 Hz, 2H), 7.63-7.58 (m, 2H), 7.50-7.38 (m, 3H), 7.17 (s, 1H), 2.23 (s, 3H), 2.22 (s, 3H); $^{13}$C NMR (100 MHz, CDCl$_3$) δ 142.9, 142.1, 138.7, 138.1, 132.9, 130.4, 129.2, 128.4, 127.5, 125.2, 20.0, 19.8; HRMS-ESI (m/z) calcd [C$_{14}$H$_{14}$O$_2$S+H]$^+$: 247.0787. found: 247.0786.

Example 7

1,4-Dimethyl-2-(phenylsulfonyl)benzene (9)

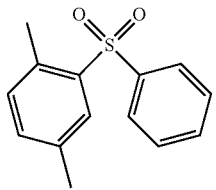 [SMILES: Cc1ccc(C)c(S(=O)(=O)c2ccccc2)c1]

Reaction Time: 8 h; Rf: 0.3 (1:4 EtOAc:Pet Ether); White solid; 20.7 mg, 55%; mp 111-113° C.;
$^1$H NMR (500 MHz, CDCl$_3$) δ 7.98 (s, 1H), 7.79 (d, J=7.6 Hz, 2H), 7.52-7.38 (m, 3H), 7.21 (d, J=7.6 Hz, 1H), 7.04 (d, J=7.6 Hz, 1H), 2.35 (s, 3H), 2.30 (s, 3H); $^{13}$C NMR (125 MHz, CDCl$_3$) δ 141.5, 138.4, 136.5, 134.8, 134.3, 132.9, 132.6, 129.7, 128.9, 127.6, 20.9, 19.7; HRMS-ESI (m/z) calcd [C$_{14}$H$_{14}$O$_2$S+H]$^+$: 247.0787. found: 247.0786.

Example 8

1-Methoxy-3-(phenylsulfonyl)benzene (11)

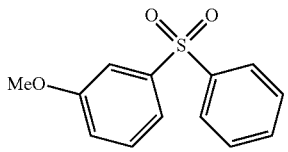 [SMILES: COc1cccc(S(=O)(=O)c2ccccc2)c1]

Reaction Time: 4 h; Rf: 0.3 (1:4 EtOAc:Pet Ether); White solid; 24.2 mg, 64%; mp 82° C.; $^1$H NMR (500 MHz, CDCl3) δ 7.88 (d, J=7.6 Hz, 2H), 7.50 (t, J=7.6 Hz, 1H), 7.46-7.40 (m, 3H), 7.38 (t, J=2.2 Hz, 1H), 7.34 (t, J=8.0 Hz, 1H), 7.01 (dd, J=2.2, 2.2 Hz, 1H), 3.77 (s, 3H); $^{13}$CNMR (125 MHz, CDCl$_3$) δ 160.0, 142.7, 141.5, 133.2, 130.4, 129.5, 127.6, 119.9, 119.5, 112.2, 55.7; HRMS-ESI (m/z) calcd [C$_{13}$H$_{12}$O$_3$S+H]$^+$: 249.0580. found: 249.0579.

Example 9

1,3-Dimethoxy-5-(phenylsulfonyl)benzene (13)

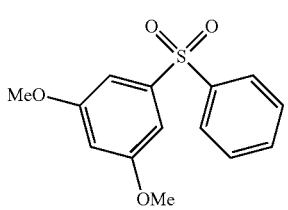 [SMILES: COc1cc(OC)cc(S(=O)(=O)c2ccccc2)c1]

Reaction Time: 4 h; Rf: 0.2 (1:4 EtOAc:Pet Ether); Yellow solid; 33.4 mg, 86%; mp 92-94° C.; $^1$H NMR (500 MHz, CDCl$_3$) δ 7.87 (d, J=7.3 Hz, 2H), 7.49 (t, J=7.6 Hz, 1H), 7.44 (t, J=7.9 Hz, 2H), 6.99 (d, J=2.8 Hz, 2H), 6.52 (t, J=2.5 Hz, 1H), 3.74 (s, 6H); $^{13}$C NMR (100 MHz, CDCl$_3$) δ 161.2, 143.3, 141.5, 133.2, 129.2, 127.6, 105.5, 105.4, 55.80; HRMS-ESI (m/z) calcd [C$_{14}$H$_{14}$O$_4$S+H]$^+$: 279.0686. found: 279.0682.

Example 10

1,2-Dimethoxy-4-(phenylsulfonyl)benzene (15)

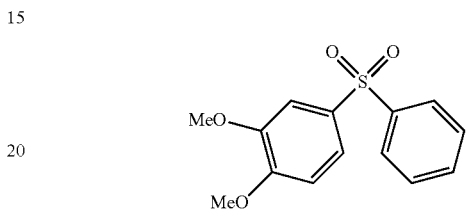

Reaction Time: 3 h; Rf: 0.4 (3:7 EtOAc:Pet Ether); Red solid; 23.3 mg, 60%; mp 118-119° C.; $^1$H NMR (400 MHz, CDCl$_3$) δ 7.85 (d, J=7.3 Hz, 2H), 7.54-7.40 (m, 4H), 7.32 (s, 1H), 6.86 (d, J=8.5 Hz, 1H), 3.85 (s, 3H), 3.84 (s, 3H); $^{13}$C NMR (100 MHz, CDCl$_3$) δ 153.0, 149.3, 142.2, 133.0, 132.9, 129.2, 127.3, 121.9, 110.8, 109.9, 56.3, 56.2; ESI-Mass (M+Na) 301. HRMS-ESI (m/z) calcd [C$_{14}$H$_{14}$O$_4$S+H]$^+$: 279.0686. found: 279.0678.

Example 11

5-(Phenylsulfonyl)benzo[d][1,3]dioxole (17)

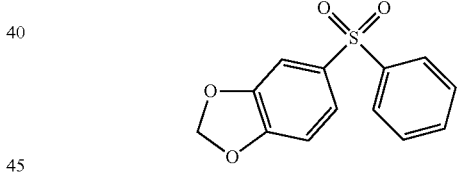

Reaction Time: 6 h; Rf: 0.2 (1:4 EtOAc:Pet Ether); White solid; 37 mg, 96%; mp 102-104° C.; $^1$H NMR (500 MHz, CDCl$_3$) δ 7.84 (d, J=7.3 Hz, 2H), 7.51-7.40 (m, 4H), 7.24 (d, J=1.8 Hz, 1H), 6.80 (d, J=8.2 Hz, 1H), 5.97 (s, 2H); $^{13}$C NMR (125 MHz, CDCl$_3$) δ 151.9, 148.4, 142.0, 134.9, 133.0, 129.2, 127.4, 123.6, 108.5, 107.8, 102.4; HRMS-ESI (m/z) calcd [C$_{13}$H$_{10}$O$_4$S+H]$^+$: 263.0373. found: 263.0371.

Example 12

(Methylsulfonyl)benzene (19)

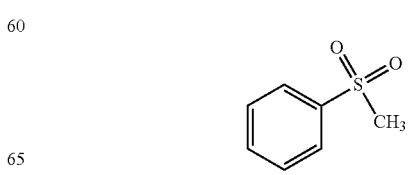

Reaction Time: 4 h; Rf: 0.2 (1:4 EtOAc:Pet Ether); Yellow solid; 19.6 mg, 75%; mp 256-258° C.; $^1$H NMR (500 MHz, CDCl$_3$) δ 7.89 (d, J=7.6 Hz, 2H), 7.60 (t, J=7.6 Hz, 1H), 7.52 (t, J=7.6 Hz, 2H), 2.99 (s, 3H); $^{13}$C NMR (125 MHz, CDCl$_3$) δ 140.6, 133.7, 129.4, 127.3, 44.5; HRMS-ESI (m/z) calcd [C$_7$H$_8$O$_2$S+H]$^+$: 157.0318. found: 157.0319.

Example 13

(Butylsulfonyl)benzene (21)

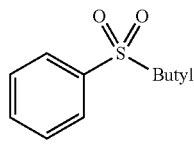

Reaction Time: 3 h; Rf: 0.5 (1:4 EtOAc:Pet Ether); thick oil; 28.9 mg, 86%; $^1$H NMR (400 MHz, CDCl$_3$) δ 7.84 (d, J=7.5 Hz, 2H), 7.59 (t, J=7.5 Hz, 1H), 7.50 (t, J=7.8 Hz, 2H), 3.02 (t, J=8.0 Hz, 2H), 1.67-1.58 (m, 2H), 1.38-1.27 (m, 2H), 0.82 (t, J=7.3 Hz, 3H); $^{13}$C NMR (100 MHz, CDCl$_3$) δ 139.2, 133.6, 129.2, 128.1, 56.1, 24.6, 21.5, 13.5; HRMS-ESI (m/z) calcd [C$_{10}$H$_{14}$O$_2$S+H]$^+$: 199.0787. found: 199.0788.

Example 14

1-Methyl-4-(phenylsulfonyl)benzene (23)

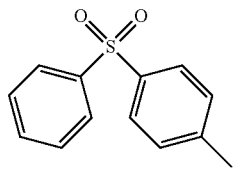 [SMILES: Cc1ccc(S(=O)(=O)c2ccccc2)cc1]

Reaction Time: 3 h; Rf: 0.5 (1:4EtOAc:Pet Ether); White solid; 26.5 mg, 68%; mp 198-200° C.; $^1$H NMR (500 MHz, CDCl$_3$) δ 7.86 (d, J=7.3 Hz, 2H), 7.47 (d, J=7.9 Hz, 2H), 7.47 (t, J=7.3 Hz, 1H), 7.42 (t, J=7.6 Hz, 2H), 7.23 (d, J=7.9 Hz, 2H), 2.32 (s, 3H); $^{13}$C NMR (100 MHz, CDCl$_3$) δ 144.1, 141.9, 138.6, 133.0, 129.9, 129.2, 127.7, 127.5, 21.5; HRMS-ESI (m/z) calcd [C$_{13}$H$_{12}$O$_2$S+H]$^+$: 233.0631. found: 233.0630.

Example 15

1-(Tert-butyl)-4-(phenylsulfonyl)benzene (25)

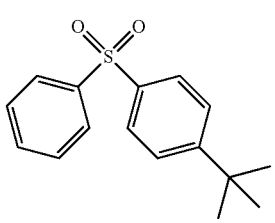 [SMILES: CC(C)(C)c1ccc(S(=O)(=O)c2ccccc2)cc1]

Reaction Time: 4 h; Rf: 0.5 (1:4 EtOAc:Pet Ether); White solid; 38.7 mg, 85%; mp 129-130° C.; $^1$H NMR (400 MHz, CDCl$_3$) δ 7.88 (d, J=7.0 Hz, 2H), 7.79 (d, J=8.8 Hz, 2H), 7.52-7.40 (m, 5H), 1.24 (s, 9H); $^{13}$C NMR (100 MHz, CDCl$_3$) δ 57.1, 141.9, 138.5, 133.0, 129.2, 127.6, 127.5, 126.3, 35.2, 31.0; HRMS-ESI (m/z) calcd [C$_{16}$H$_{18}$O$_2$S+H]$^+$: 275.1100. found: 275.1099.

Example 16

1-Methoxy-4-(phenylsulfonyl)benzene (27)

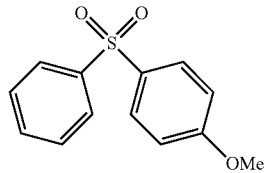 [SMILES: COc1ccc(S(=O)(=O)c2ccccc2)cc1]

Reaction Time: 1 h; Rf: 0.2 (1:4 EtOAc:Pet Ether); White solid; 25.4 mg, 61%; mp 90-91° C.; $^1$H NMR (400 MHz, CDCl$_3$) δ 7.87-7.78 (m, 4H), 7.50-7.38 (m, 3H), 6.92-6.87 (m, 2H), 3.77 (s, 3H); $^{13}$C NMR (100 MHz, CDCl$_3$) δ 163.3, 142.3, 133.1, 132.8, 129.9, 129.2, 127.3, 114.5, 55.6; HRMS-ESI (m/z) calcd [C$_{13}$H$_{12}$O$_3$S+H]$^+$: 249.0580. found: 249.0579.

Example 17

1-(4-(phenylsulfonyl)phenyl)ethan-1-one (29)

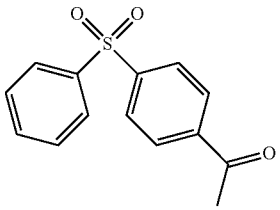 [SMILES: CC(=O)c1ccc(S(=O)(=O)c2ccccc2)cc1]

Reaction Time: 4 h; Rf: 0.2 (1:4 EtOAc:Pet Ether); Yellow solid; 22.5 mg, 54%; mp 132-134° C.; $^1$H NMR (400 MHz, CDCl$_3$) δ 7.98 (s, 4H), 7.89 (d, J=8.5 Hz, 2H), 7.53 (t, J=8.5 Hz, 1H), 7.46 (t, J=8.5 Hz, 2H), 2.55 (s, 3H); $^{13}$C NMR (100 MHz, CDCl$_3$) δ 196.7, 145.4, 140.7, 140.3, 133.6, 129.5, 129.0, 128.0, 127.8, 26.9; ESI-Mass (M+1) 261. HRMS-ESI (m/z) calcd [C$_{14}$H$_{12}$O$_3$S+H]$^+$: 261.0580. found: 261.0573.

Example 18

1-Nitro-4-(phenylsulfonyl)benzene (31)

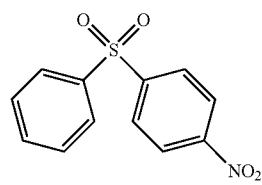 [SMILES: O=[N+]([O-])c1ccc(S(=O)(=O)c2ccccc2)cc1]

Reaction Time: 3 h; Rf: 0.5 (1:4 EtOAc:Pet Ether); White solid; 32.6 mg, 74%; mp 144-145° C. $^1$H NMR (400 MHz, CDCl$_3$) δ 8.28 (d, J=9 Hz, 2H), 8.07 (d, J=9 Hz, 2H), 7.90 (d, J=7.3 Hz, 2H), 7.57 (t, J=7.3 Hz, 1H), 7.49 (t, J=7.3 Hz, 2H); $^{13}$C NMR (100 MHz, CDCl$_3$) δ 150.3, 147.3, 140.0, 134.1, 129.7, 129.0, 128.0, 124.5; ESI-Mass (M+Na) 209;

Example 19

1-Fluoro-4-(phenylsulfonyl)benzene (33)

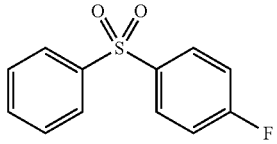 [SMILES: O=S(=O)(c1ccccc1)c1ccc(F)cc1]

Reaction Time: 3 h; Rf: 0.5 (1:4 EtOAc:Pet Ether); White solid; 34 mg, 86%; mp 113-115° C.; $^1$H NMR (500 MHz, CDCl$_3$) δ 7.93-7.83, (m, 4H), 7.55-7.41 (m, 3H), 7.22-7.08 (m, 2H); $^{13}$C NMR (100 MHz, CDCl$_3$) δ 165.4 (d, J=255.8 Hz), 141.5, 137.7, 133.3, 130.5 (d, J=9.2 Hz), 129.4, 127.6, 116.6 (d, J=32.1 Hz); HRMS-ESI (m/z) calcd [C$_{12}$H$_9$O$_2$SF+H]$^+$: 237.0380. found: 237.0379.

Example 20

2-bromo-5-(phenylsulfonyl)thiophene (35)

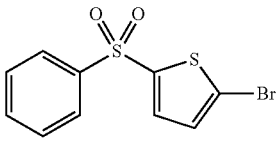 [SMILES: O=S(=O)(c1ccccc1)c1ccc(Br)s1]

Reaction Time: 3 h; Rf: 0.5 (1:4 EtOAc:Pet Ether); White solid; 37.09 mg, 73%; mp 105-107° C.; 1H NMR (400 MHz, CDCl$_3$) δ 7.90 (d, J=6.8 Hz, 2H), 7.54 (t, J=7.7 Hz, 1H), 7.46 (t, J=7.5 Hz, 2H), 7.39 (d, J=4.1 Hz, 1H), 6.99 (d, J=4.1 Hz, 1H); $^{13}$C NMR (100 MHz, CDCl$_3$) δ 143.8, 141.5, 133.6, 133.4, 130.8, 129.5, 127.3, 122.1; HRMS-ESI (m/z) calcd C$_{10}$H$_7$O$_2$S$_2$$^{81}$Br+Na]$^+$: 326.8943. found: 326.8936.

ADVANTAGES OF THE INVENTION

The process of the invention works with very simple reagents at very mild reaction condition which can be very useful industrially. Also the process can be applied for large scale synthesis.

The invention claimed is:

1. A room temperature single step process for synthesis of compound of Formula I

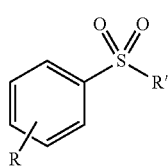

Formula I wherein, R is selected from H, alkyl (C$_1$-C$_6$), aryl, heteroaryl, O-, S-, N-, P-alkyl/unsubstituted and substituted aryl;

R' is selected from alkyl (C$_1$-C$_6$), aryl, heteroaryl, O-, S-, N-, P-alkyl/unsubstituted and substituted aryl;

comprising the steps of:

a. adding benzyne precursor of Formula II to a stirred solution of fluoride ion source and compound of Formula III in the ratio ranging between 1:1 to 1:1.1 in anhydrous acetonitrile to obtain a reaction mixture;

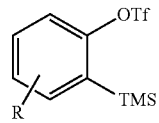

Formula II

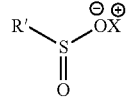

Formula III wherein, R is selected from H, alkyl, aryl, heteroaryl, O-, S-, N-, P-alkyl/unsubstituted and substituted aryl;

R' is selected from, alkyl, aryl, heteroaryl, O-, S-, N-, P-alkyl/unsubstituted and substituted aryl;

X is selected from H, Li, Na, K, Cs;

b. stirring the reaction mixture of step (a) for the period in the range of 1 to 8 hours followed by purification to obtain the desired product I.

2. The process according to claim 1, wherein the fluoride ion source is selected from the group consisting of TBAF (Tetra-n-butylammonium fluoride), CsF (Cesium fluoride), NaF (Sodium Fluoride), RbF (Rubidium fluoride) or KF (Potassium fluoride).

3. The process according to claim 1, wherein the fluoride ion source is selected from TBAF or CsF.

4. The process according to claim 1, wherein the compound of formula I is selected from the group consisting of:
1-Phenyl (sulfonyl)benzene (3);
1,2-Difluoro-4-(phenylsulfonyl)benzene (5);
1,2-Dimethyl-4-(phenylsulfonyl)benzene (7);
1,4-Dimethyl-2-(phenylsulfonyl)benzene (9);
1-Methoxy-3-(phenylsulfonyl)benzene (11);
1,3-Dimethoxy-5-(phenylsulfonyl)benzene (13);
1,2-Dimethoxy-4-(phenylsulfonyl)benzene (15);
5-(Phenylsulfonyl)benzo[d][1,3]dioxole (17);
(Methylsulfonyl)benzene (19);
(Butylsulfonyl)benzene (21);
1-Methyl-4-(phenylsulfonyl)benzene (23);
1-(Tert-butyl)-4-(phenylsulfonyl)benzene (25);
1-Methoxy-4-(phenylsulfonyl)benzene (27);
1-(4-(phenylsulfonyl)phenyl)ethan-1-one (29);
1-Nitro-4-(phenylsulfonyl)benzene (31);
1-Fluoro-4-(phenylsulfonyl)benzene (33) and;
2-bromo-5-(phenylsulfonyl)thiophene (35).

5. The process according to claim 1, wherein the compound of formula II is selected from the group consisting of:
2-(trimethylsilyl)phenyl trifluoromethane-sulfonate (1)
4,5-difluoro-2-(trimethylsilyl)phenyl trifluoromethane-sulfonate (4)
4,5-dimethyl-2-(trimethylsilyl)phenyl trifluoromethane-sulfonate (6)

3,6-dimethyl-2-(trimethylsilyl)phenyl trifluoromethane-sulfonate (8)

3-methoxy-2-(trimethylsilyl)phenyl trifluoromethane-sulfonate (10)

3,5-dimethoxy-2-(trimethylsilyl)phenyl trifluoromethane-sulfonate (12)

4,5-dimethoxy-2-(trimethylsilyl)phenyl trifluoromethane-sulfonate (14) and 6-(trimethylsilyl)benzo[d][1,3]dioxol-5-yl trifluoromethane-sulfonate (16).

6. The process according to claim 1, wherein the compound of formula III is selected from the group consisting of:

sodium benzenesulfinate (2)
sodium methanesulfinate (18)
sodium butane-1-sulfinate (20)
sodium 4-methylbenzenesulfinate (22)
sodium 4-(tert-butyl)benzenesulfinate (24)
sodium 4-methoxybenzenesulfinate (26)
sodium 4-acetylbenzenesulfinate (28)
sodium 4-nitrobenzenesulfinate (30)
sodium 4-fluorobenzenesulfinate (32) and
Sodium 5-bromothiophene-2-sulfinate (34).

7. The process according to claim 1, wherein the yield of the compound of formula I is in the range of 45-96%.

* * * * *